United States Patent [19]

Wiegel

[11] Patent Number: 6,107,034
[45] Date of Patent: Aug. 22, 2000

[54] GATA-3 EXPRESSION IN HUMAN BREAST CARCINOMA

[75] Inventor: Ronald J. Wiegel, Woodside, Calif.

[73] Assignee: The Board of Trustees of the Leland Stanford Junior University, Palo Alto, Calif.

[21] Appl. No.: 09/037,135

[22] Filed: Mar. 9, 1998

[51] Int. Cl.$^7$ .................................................. C12Q 1/68
[52] U.S. Cl. .................................................................. 435/6
[58] Field of Search ........................................ 435/6, 7.1

[56] References Cited

PUBLICATIONS

Hoch et al., Int. J. Cancer, vol. 84, pp 122–128, 1999.
Bargou, Ralf C., et al., "Nuclear Localization and Increased levels of Transcription Factor YB–1 In Primary Human Breast Cancers Are Associated With Intrinsic MDR1 Gene Expression," *Nature Medicine* (Apr. 1997) vol. 3, No. 4:447–450.
Labastie, M.C., et al., "Structure and Expression of The Human GATA3 Gene," *Genomics* (1994) vol. 21:1–6.
Marine, Joseph, et al., "The Human Enhancer–Binding Protein Gata3 Binds To Several T–Cell Recepter Regulatory Elements," *Proc. Natl. Acad. Sci. USA* (Aug. 1991) vol. 88:7284–7288.
Piao, Yun–Shang, et al., "The Proximal Promoter Region of the Gene Encoding Human 17 β–Hydroxysteroid Dehydrogenase Type 1 Contains GATA, AP–2, and Sp1 Response Elements: Analysis of Promoter Function in Choriocarcinoma Cells," *Endocrinology* (1997) vol. 138, No. 8:3417–3425.
Ponglikitmongkol, Mathurose, et al., "Genomic Organization of the Human Oestrogen Receptor Gene," *The EMBO Journal* (1988) vol. 7, No. 11:3385–3388.
Tang, Zuoquin, et al., "A Transcriptional Enhancer Required for the Differential Expression of the human Estrogen Receptor in Breast Cancers," *Molecular and Cellular Biology* (Mar. 1997) vol. 17, No. 3:1274–1280.
Watson, CJ, et al., "Elevated Levels of Members of the STAT Family of Transcription Factors In Breast Carcinoma Nuclear Extracts," *Br. J. Cancer* (1995) vol. 71, No. 4:840–844.

*Primary Examiner*—W. Gary Jones
*Assistant Examiner*—Jehanne Souaya
*Attorney, Agent, or Firm*—Bozicevic, Field & Francis; Pamela Sherwood

[57] ABSTRACT

A highly statistically significant correlation between ER and GATA-3 expression in breast cancers is demonstrated. Detection of GATA-3 in breast carcinoma samples provides a diagnostic test for a hormone responsive tumor. Screening for pharmacologic agents and molecular targets utilizes the GATA-3 association with breast carcinoma.

7 Claims, 3 Drawing Sheets

GATA-3 EXPRESSION IN HUMAN BREAST CARCINOMA

INTRODUCTION

The transformation and malignant growth of tumor cells is a complex process, which can be variable even within a particular tissue. Analytical methods that can define the phenotype of tumor cells are useful in determining appropriate therapy, and are therefore of clinical interest.

The expression of estrogen receptor (ER) has been shown to have important implications for the biology of breast carcinomas. Patients with tumors that express ER have a longer disease-free interval and overall survival than patients with tumors that lack ER expression. ER-positive tumors are more likely to occur in post-menopausal women whereas ER-negative breast cancers occur more frequently in young women. Breast cancers that express ER are usually well-differentiated tumors that respond to hormonal therapy compared to poorly differentiated, ER-negative tumors that are hormone unresponsive. However, the association between ER expression and hormone responsiveness is not perfect; approximately 15–25% of ER-positive tumors are not hormone responsive and 5–15% of ER-negative tumors respond to hormonal therapy.

One hypothesis is that there are a set of genes expressed in association with ER that are critical for establishing the hormone responsive breast cancer phenotype. In this model, ER is a marker for a well-differentiated, hormone responsive carcinoma. Although ER is likely to be important to hormone response through the regulation of estradiol-responsive genes, the expression of an additional set of genes that are not part of the estradiol-response pathway are important to establishing the hormone responsive phenotype. One experiment in support of this hypothesis is the finding that introducing functional ER expression in ER-negative breast carcinomas by transfection generates a cell with paradoxical responses to estradiol.

In addition, studies of the ER gene promoter have identified intrinsic differences in the repertoire of transcription factors comparing ER-positive and ER-negative cell lines. Both AP-1 and ERF-1/AP-2γ transcription factors have been implicated in regulating ER expression in breast cancer and these transcriptional activities appear to be specific to ER-positive tumors. Watson and Miller (1995) *Br J Cancer* 71(4):840–844 analyzed breast carcinoma nuclear extracts and found elevated levels of members of the STAT family of transcription factors, including Stat1 and possibly Stat3. Bargou et al. (1997) *Nat Med* 3(4):447–450 describe nuclear localization and increased levels of transcription factor YB-1 in primary human breast cancers, and an association with intrinsic MDR1 gene expression. In multidrug-resistant MCF-7 breast cancer cells, nuclear localization of YB-1 is associated with MDR-1 gene expression.

Ponglikitmongkol et al. (1988) *EMBO J* 7(11):3385–3388 describe the genomic organization of the human estrogen receptor gene. Tang et al. (1997) *Mol Cell Biol* 17(3):1274–1280 identified a transcriptional enhancer in the human ER gene which is differentially active in ER-positive (ER+) and ER-negative (ER−) human breast cancer cell lines. Enhancer function was mapped to a 35-bp element upstream of the major human ER mRNA start site, and DNA-protein complexes were identified which specifically form on this enhancer.

The molecular basis for the association between ER expression, hormonal responsiveness and breast cancer prognosis is not clear. Differences in trans-acting factors may regulate a set of genes, in addition to ER, that are important to establishing the hormone responsive phenotype. Determination of the underlying basis for differential prognosis between ER positive and ER native breast carcinomas would allow better patient evaluation, and provide a target for future therapy. Such a diagnostic test would be of great benefit to patients and clinicians.

Relevant Literature

GATA-3 is a member of the GATA family of transcription factors, which are zinc-finger transcription factors that regulate gene expression by binding to the consensus DNA sequence A/T GATA A/G. GATA-3 is abundantly expressed in the T-lymphocyte lineage and is thought to participate in T-cell receptor gene activation through binding to enhancers. Labastie et al. (1994) *Genomics* 21(1):1–6 cloned the human gene. Its 2 zinc fingers are encoded by 2 separate exons highly conserved with those of GATA-1, but there are no other structural homologies between the two genes. Joulin et al. (1991) mapped the human GATA-3 gene to 10p15 by in situ hybridization.

Marine and Winoto (1991) *Proc Natl Acad Sci U S A* 88(16):7284–7288 investigated human GATA-3, and demonstrate that it binds to several T-cell receptor regulatory elements. Piao et al. (1997) *Endocrinology* 138(8):3417–3425 analyzed the proximal promoter region of the gene encoding human 17 beta-hydroxysteroid dehydrogenase type 1, and found that it contains GATA, AP-2, and Sp1 response element. GATA-3 apparently acted as a negative control element for HSD17B1 transcription.

SUMMARY OF THE INVENTION

The transcription factor GATA-3 is shown to expressed in estrogen receptor positive breast carcinoma cells. Detection of GATA-3 expression in breast carcinomas is useful as a diagnostic, for determining the effectiveness of drugs, and determining patient prognosis. GATA-3 further provides a target for screening pharmaceutical agents that may act against carcinomas.

DESCRIPTION OF THE SPECIFIC EMBODIMENTS

Figure 1:
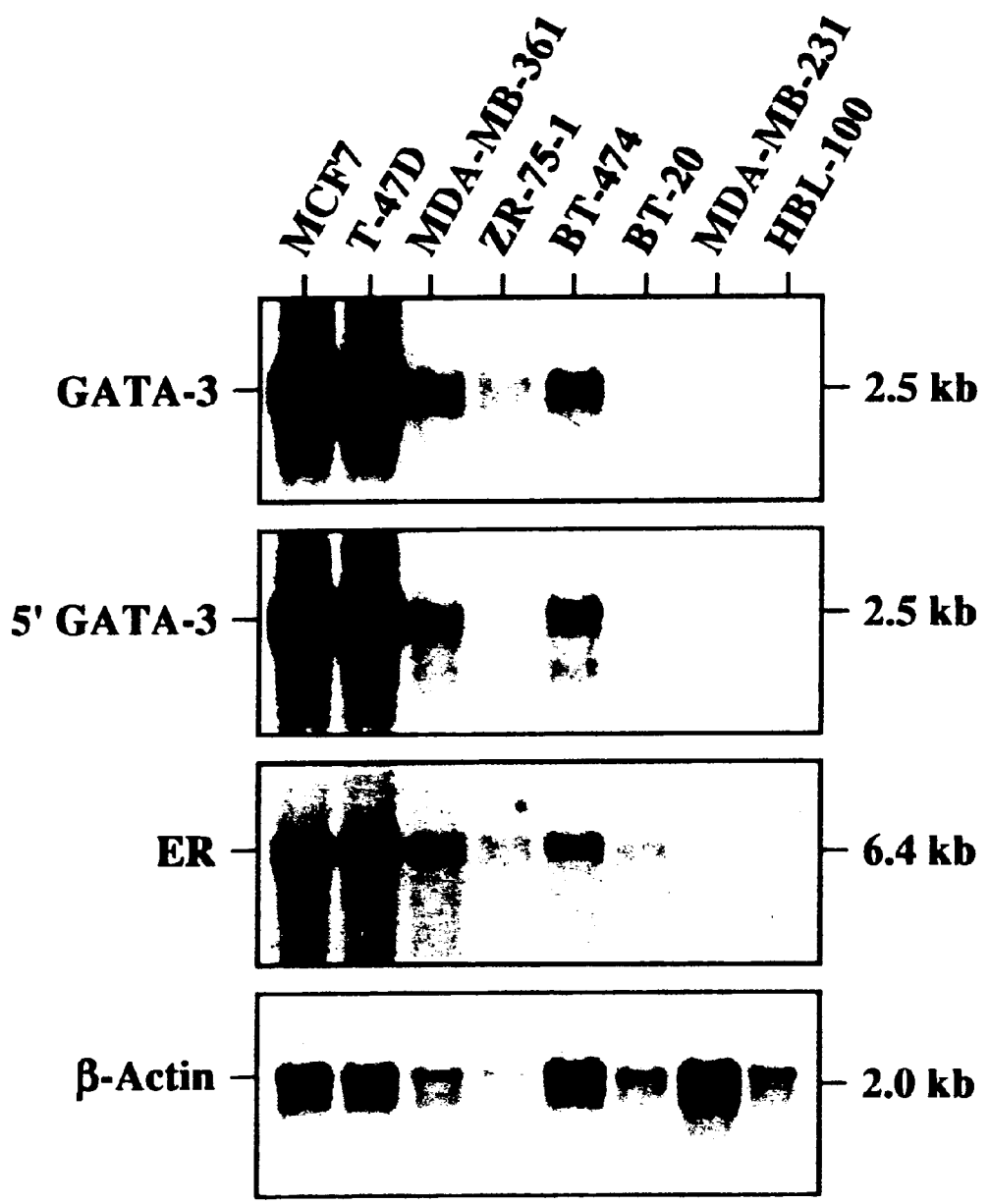
FIG. 1 is a northern blot showing GATA-3 expression in breast carcinoma cells lines.

Methods are provided for determining whether cells in a breast carcinoma sample will have a hormone responsive phenotype. The transcription factor GATA-3 is shown to be associated with estrogen receptor positive breast carcinoma cells. Detection of GATA-3 expression in breast carcinomas provides a useful diagnostic for predicting patient prognosis and probability of drug effectiveness. GATA3 provides a target for drug screening, and for determining other molecular targets involved in the hormone responsive phenotype.

The expression of ER in primary breast carcinomas identifies a tumor phenotype that is associated with hormone responsiveness, longer disease-free interval and longer overall survival. A highly statistically significant correlation is shown between ER and GATA-3 expression in breast cancers. In addition, GATA-3 is not estradiol responsive, demonstrating genes regulated independently of estradiol that are important for establishing the more favorable breast cancer phenotype associated with ER expression. This association indicates an important functional role for GATA-3 in hormone-responsive breast cancers. GATA-3 has not previously been described in normal breast or breast carcinomas. Since GATA-3 is known to be a transcription factor, the striking pattern of expression in ER-positive tumors indicates that target genes regulated by GATA-3 are critical to the hormone-responsive breast cancer phenotype.

DIAGNOSTIC METHODS

Breast carcinomas are roughly divided into two classes. The first class, herein termed "responsive", is characterized by longer disease-free interval and longer overall survival. Usually these cells express the estrogen receptor; and can be treated by such agents as docetaxel, paclitaxel, and other taxanes. Responsive carcinomas express GATA-3. The second class, herein termed "unresponsive" are poorly differentiated, do not respond to hormonal therapy, and carry a worse overall prognosis. Non-responsive carcinomas lack GATA-3 expression. Methods of determining which class a patient sample falls in allows better therapeutic decisions.

Determination of whether a patient sample is of a responsive or non-responsive phenotype can be performed by typing the cells for the expression of GATA-3. Detection of the presence of GATA-3 is performed by protein, DNA or RNA sequence and/or hybridization analysis of a patient sample. Generally the sample will be a biopsy or other cell sample from the tumor. Where the tumor has metastasized, blood samples may be analyzed if care is taken to exclude T cells and other contaminating lymphocytes from the sample.

Specific Binding Members

In a typical assay, a carcinoma sample is assayed for the presence of GATA-3 specific sequences by combining the sample with a GATA-3 specific binding member, and detecting directly or indirectly the presence of the complex formed between the two members. The term "specific binding member" as used herein refers to a member of a specific binding pair, i.e. two molecules where one of the molecules through chemical or physical means specifically binds to the other molecule. In this particular case one of the molecules is GATA-3, where GATA-3 is any protein substantially similar to the amino acid sequence provided in SEQ ID NO:1, or a fragment thereof. The complementary members of a specific binding pair are sometimes referred to as a ligand and receptor.

In addition to antigen and antibody specific binding pairs, peptide-MHC antigen and T cell receptor pairs; complementary nucleotide sequences (including nucleic acid sequences used as probes and capture agents in DNA hybridization assays); peptide ligands and receptor, where at least one ligand of GATA-3 is the DNA motif recognized by the protein; autologous monoclonal antibodies, and the like. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc. so long as an epitope is present.

Immunological specific binding pairs include antigens and antigen specific antibodies or T cell antigen receptors. Recombinant DNA methods or peptide synthesis may be used to produce chimeric, truncated, or single chain analogs of either member of the binding pair, where chimeric proteins may provide mixture(s) or fragment(s) thereof, or a mixture of an antibody and other specific binding members. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Monoclonal antibodies specific for GATA-3 are described in Yang et al. (1994) *Mol Cell Biol* 14(3):2201–2212; and Elefanty et al. (1996) *EMBO J* 15(2):319–333, which describe their use in indirect immunofluorescent histochemistry, and immunoelectron microscopy.

Alternatively, monoclonal or polyclonal antibodies are raised to human GATA-3. The antibodies may be produced in accordance with conventional ways, immunization of a mammalian host, e.g. mouse, rat, guinea pig, cat, dog, etc., fusion of resulting splenocytes with a fusion partner for immortalization and screening for antibodies having the desired affinity to provide monoclonal antibodies having a particular specificity. These antibodies can be used for affinity chromatography, ELISA, RIA, and the like. The antibodies may be labeled with radioisotopes, enzymes, fluorescers, chemiluminescers, or other label which will allow for detection of complex formation between the labeled antibody and its complementary epitope.

Generally the amount of bound GATA-3 detected will be compared to negative control samples from normal tissue or from known non-responsive carcinoma cells. The presence of increased levels of GATA-3 specific binding is indicative of a responsive tumor phenotype, usually at least about a 5 fold increase will be taken as a positive reaction.

Nucleic acid sequences for detection may be complementary to a GATA-3 sequence, or may have the recognition motif A/T GATA A/G (SEQ ID NO:2). Nucleic acids complementary to GATA-3 may be cDNA, mRNA or genomic DNA, or a fragment thereof. Fragments may be obtained of the DNA sequence by chemically synthesizing oligonucleotides in accordance with conventional methods, by restriction enzyme digestion, by PCR amplification, etc. For the most part, DNA fragments will be of at least 25 nt, usually at least 30 nt, more usually at least about 50 nt. Such small DNA fragments are useful as primers for PCR, hybridization screening, etc.

Where it is desirable to generate probes or primers that distinguish GATA-3 from other GATA transcription factor sequences, the probe may be derived from the less conserved region of the genes. Such sequences include the 3' and 5' untranslated region of the cDNA.

For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

For hybridization probes, it may be desirable to use nucleic acid analogs, in order to improve the stability and binding affinity. The term "nucleic acid" shall be understood to encompass such analogs. A number of modifications have been described that alter the chemistry of the phosphodiester backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire phosphodiester backbone with a peptide linkage. Sugar modifications are also used to enhance stability and affinity. The a-anomer of deoxyribose may be used, where the base is inverted with respect to the natural b-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Nucleic Acid Analysis

A number of methods are available for analyzing nucleic acids for the presence or absence of a specific sequence. For analysis based on nucleic acids, mRNA or nucleic acids derived therefrom are analyzed for the presence of GATA-3 specific sequences. The complete cDNA sequence of human GATA-3 is provided for convenience as SEQ ID NO:1. mRNA in a sample may be used directly, or may be reverse transcribed to generate a cDNA strand. The cDNA may be amplified by conventional techniques, such as the polymerase chain reaction (PCR), to provide sufficient amounts for analysis. The use of the polymerase chain reaction is described in Saiki, et al. (1985) *Science* 239:487, and a review of current techniques may be found in Sambrook, et al. *Molecular Cloning: A Laboratory Manual*, CSH Press 1989, pp.14.2–14.33. Amplification may also be used to determine whether a specific sequence is present, by using a primer that will specifically bind to the desired sequence, where the presence of an amplification product is indicative that a specific binding complex was formed. Alternatively, the mRNA sample is fractionated by electrophoresis, e.g. capillary or gel electrophoresis, transferred to a suitable support, e.g. nitrocellulose and then probed with a fragment of the GATA-3 sequence. Other techniques may also find use, including oligonucleotide ligation assays, binding to solid state arrays, etc. Detection of mRNA having the subject sequence is indicative of GATA-3 gene expression in the sample.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine(ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. mRNA or amplification product, is analyzed by one of a number of methods known in the art. Hybridization with a GATA-3 specific sequence may be used to determine its presence, by northern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detection. For examples of arrays, see Hacia et al. (1996) *Nature Genetics* 14:441–447; Lockhart et al. (1996) *Nature Biotechnol.* 14:1675–1680; and De Risi et al. (1996) *Nature Genetics* 14:457–460.

Polypeptide Analysis

Screening may also be based on the functional or antigenic characteristics of the protein, e.g. immunoassays, determination of GATA-3 directed transcription, binding to a GATA-3 DNA motif, etc.

A sample is taken from a patient with breast carcinoma. Samples, as used herein, include biological fluids such as blood; organ or tissue culture derived fluids; etc. Biopsy samples or other sources of carcinoma cells are of particular interest, e.g. tumor biopsy, etc. Also included in the term are derivatives and fractions of such cells and fluids. The number of cells in a sample will generally be at least about $10^3$, usually at least $10^4$, and may be about $10^5$ or more. The cells may be dissociated, in the case of solid tissues, or tissue sections may be analyzed. Alternatively a lysate of the cells may be prepared.

Detection may utilize staining of cells or histological sections, performed in accordance with conventional methods. The antibodies or other specific binding members of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and GATA-3 in a lysate. Measuring the concentration of GATA-3 binding in a sample or fraction thereof may be accomplished by a variety of specific assays. A conventional sandwich type assay may be used. For example, a sandwich assay may first attach GATA-3 specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g.

polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of GATA-3 is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing a second antibody is applied. The antibody will bind GATA-3 with sufficient specificity such that it can be distinguished from other components present. The second antibodies may be labeled to facilitate direct, or indirect quantification of binding. Examples of labels that permit direct measurement of second receptor binding include radiolabels, such as $^3H$ or $^{125}I$, fluorescers, dyes, beads, chemilumninescers, colloidal particles, and the like. Examples of labels that permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material, leaving the specific complex formed between GATA-3 and the specific binding member. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for GATA-3 as desired, conveniently using a labeling method as described for the sandwich assay.

Other diagnostic assays of interest are based on the functional properties of GATA-3 proteins. For example, a functional assay may be based on the transcriptional changes mediated by GATA-3 gene products. Other assays may, for example, detect DNA footprinting changes due to complexes formed between GATA-3 and its binding motif.

In some cases, a competitive assay will be used. In addition to the patient sample, a competitor to GATA-3 is added to the reaction mix. The competitor and the GATA-3 compete for binding to the specific binding partner. Usually, the competitor molecule will be labeled and detected as previously described, where the amount of competitor binding will be proportional to the amount of GATA-3 present. The concentration of competitor molecule will be from about 10 times the maximum anticipated GATA-3 concentration to about equal concentration in order to make the most sensitive and linear range of detection.

It is particularly convenient in a clinical setting to perform the immunoassay in a self-contained apparatus. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it a conjugate of an enzyme with a GATA-3 specific antibody.

SCREENING METHODS

The GATA-3 specific reagents are used to identify targets of GATA-3 in breast carcinomas. For example, GATA-3 may be introduced into a non-responsive carcinoma using an inducible expression system. Suitable positive and negative controls are included. Transient transfection assays, e.g. using adenovirus vectors, may be performed. The cell system allows a comparison of the pattern of gene expression in non-responsive cells with or without GATA-3 expression.ABOVE gene expression of putative target genes may be monitored by Northern blot or by probing microarrays of candidate genes with the test sample and a negative control where GATA-3 is not induced. To identify down-regulated genes will require switching the negative control with the induced sample RNAs.

Some of the potential target genes of GATA-3 identified by this method will be secondary or tertiary in a complex cascade of gene expression induced by GATA-3. To identify primary targets of GATA-3 activation, expression will be examined early after GATA-3 induction (within 1–2 hours) or after blocking later steps in the cascade with cycloheximide.

Target genes identified by this method may be analyzed for expression in primary patient carcinomas as well. The data for GATA-3 and target gene expression may be analyzed using statistical analysis in a manner similar to the data presented in Table 1 in order to establish a correlation between GATA-3 and target gene expression in primary breast tumors.

The subject methods are also used to determine the functional consequences of GATA-3 expression influencing the responsive breast cancer phenotype through the regulation of a set of target genes. Normally, ER-positive cells increase proliferation in response to estradiol, whereas, ER-negative cells transfected with ER are growth suppressed by estradiol treatment. GATA-3 may allow ER to function as expected for normal ER-positive breast carcinoma cells. Since the function of GATA-3 is to induce target gene expression, the physiologic role of GATA-3 is likely to be mediated through the effects of target genes.

GATA-3 can be used to induce or significantly modulate the hormone responsiveness of breast cancers. Expression of GATA-3 is up-regulated through administration of agents that induce its expression, or through the introduction of GATA-3 expression vectors into poorly differentiated, ER-negative tumors.

Drug screening identifies agents that mimic, modulate or reverse the function of GATA-3. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions.

The complexes that are formed with GATA-3 and DNA are disrupted by chemotherapeutic agents, such as tamoxifen. Drug screening may be performed with the DNA-protein complexes to determine if a candidate agent is capable of disrupting the complexes. An assay of interest determines the ability of a candidate agent to mimic the effects of tamoxifen in disrupting GATA-3 complexes. Such agents may find use in chemotherapy against responsive breast carcinomas.

The term "agent" as used herein describes any molecule, e.g. protein or pharmaceutical, with the capability of altering or mimicking the physiological function of a target protein. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of cancer, etc., or to otherwise enhance GATA-3 function. The agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The agents of the present invention can be used in native form or can be modified to form a chemical derivative. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of present invention can be administered concurrently with, prior to, or following the administration of the other agent.

The agents of the present invention are administered to the mammal in a pharmaceutically acceptable form and in a therapeutically effective concentration. A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The agents of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable composition suitable for effective administration, such compositions will contain an effective amount of one or more of the agents of the present invention, together with a suitable amount of carrier vehicle.

Additional pharmaceutical methods may be employed to control the duration of action. Control release preparations may be achieved through the use of polymers to complex or absorb one or more of the agents of the present invention. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate agents of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization,for example, hydroxymethylcelluloseor gelatine microcapsules; and poly(methylmethacylate) microcapsules, respectively, or in colloidal drug delivery systems, for example, liposomes, albumin microspheres, microemulsions, nanoparticles, and nanocapsules or in macroemulsions.

The following examples are offered by way of illustration and not by way of limitation.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Experimental Procedures

Cell Lines.

All cell lines were obtained from American Type Culture Collection (ATCC, Rockville, Md.) and were maintained as described previously. MCF7 cells that were induced with estradiol were grown under normal conditions until approximately 25% confluence. The media was subsequently changed to phenol-red free Minimal Essential Media (Gibco BRL, Gaithersburg, Md.) supplemented with 10% charcoal-stripped fetal calf serum, 10 U/ml penicillin G, 10 µg/ml streptomycin, 6 ng/ml bovine insulin for six days. MCF7 cells were induced with $1 \times 10^{-8}$ M water soluble β-estradiol (Sigma Chemical Company, St. Louis, Mo.) for three days.

Screening the Atlas™ Human cDNA Expression Array.

To probe the Atlas™ Human cDNA Expression Array (Clontech, Palo Alto, Calif.), poly(A+)RNA from cell lines MCF7, T-7D, MDA-MB-231, and HBL-100 was isolated using the PureRNA Isolation Kit (Clontech). The Atlas™ Human cDNA Expression Array was screened in a collaboration with Clontech according to the conditions outlined in the product manual.

Isolation of Poly(A+)RNA and Northern Blot Analysis.

Poly(A+)mRNA was isolated from breast carcinoma cell lines and analyzed by Northern blot as described previously (Carmeci et al. (1997) *Genomics* 45, 607–617). The GATA-3 cDNA probe was prepared by reverse transcribing 1.6 µg of MCF7 poly(A)+RNA using the GeneAmp® RNA PCR Kit (Perkin Elmer, Foster City, Calif.) as per the manufacturer's recommendations. Resultant cDNA was used as template to PCR amplify (GeneAmp® PCR Kit, Perkin Elmer) the region of the GATA-3 cDNA from +530 to +1712 (numbered in accordance with the GATA-3 cDNA sequence, Genbank accession number X55122) using primers GATA3-2 (SEQ ID NO:3) [5-CCTGGAATCTCAGCCCCTTC-3'] and GATA3-4 (SEQ ID NO:4) [5'-GTTGGAACACAGACACCACAG-3']. A GATA-3 probe (5' GATA-3) corresponding to the 5' untranslated region of the GATA-3 cDNA was prepared by PCR amplifying the segment from +28 to +195 using primers GATA3-8 (SEQ ID NO:5) [5'-CCTTCTCCTTTGCTCACCTTTGCTTC-3'] and GATA3-9 (SEQ ID NO:6) [5'-CTCGGCTGTGCTCGCGCCCTCTCGCC-3']. The PCR products were gel purified and $^{32}$P-labeled for probes as described previously (Carmeci et al. supra.) Northern blots were sequentially stripped and re-hybridized using ER, pS2 and β-actin probes.

Screening MCF7 cDNA Library for GATA-3.

Approximately $1 \times 10^6$ plaques from an MCF7 cDNA library (Thompson et al. (1997) *J. Steroid Biochem. Molec. Biol.* 62, 143–153) were screened using the 1182 bp GATA-3 fragment generated with the primers GATA3-2 and GATA3-4 (as described above). The screening, hybridization, and plaque purification conditions used have been described previously (Thompson et al., supra.)

Sequencing Analysis.

Sequencing was performed on double-stranded templates using the dideoxynucleotide chain-termination method with [α-$^{35}$S] dATP, 1000 Ci/mmol (Amersham). Sequencing reactions were carried out with the Sequenase™ version 2.0 T7 DNA polymerase sequencing Kit (USB, Cleveland, Ohio) with T3 and T7 primers (Promega, Madison, Wis.).

In Vitro Transcription and Translation.

The complete coding region of the GATA-3 cDNA was amplified by PCR from +183 (transcriptional start site is at +199) to +1549 using the primers GATA3-5 Eco (SEQ ID NO:7) [5'-GGGGAATTCAGCCGAGGCCATGGAGGTGACGGCGG-3'] and GATA3-3 Xho (SEQ ID NO:8) [5'-AGCCTCGAGCAGGGCTCTAACCCATGGCGG-3'] (Advantage™ cDNA PCR kit, Clontech). The PCR product was cloned into the pCR™II vector using the Original TA Cloning® Kit (Invitrogen® Corp., Carlsbad, Calif.). The resultant plasmid (TA/GATA3) was used as the DNA template for in vitro transcription and translation using the SP6 TNT Coupled Reticulocyte Lysate System (Promega) according to the manufacturer's non-radioactive protocol.

Gel Retardation Assay.

Nuclear extracts were prepared according to the method of Dignam et al. (1983) *Nucl. Acids Res* 11, 1475–1489. For gel retardation assays with the in vitro transcribed/translated GATA-3, 2 µl of TNT-GATA-3 product were used in each 25 µl reaction. Probe for the gel shift assay was prepared using a double-stranded wild type GATA consensus oligonucleotide (SEQ ID NO:9) [5'-CACTTGATAACAGAAAGTGATAACTCT-3'] (Santa Cruz Biotechnology, Santa Cruz, Calif.) labeled as described previously (deConinck et al. (1995) *Mol. Cell. Biol.* 15, 2191–2196). Gel shift reactions were performed as described previously (deConinck et al., supra.) For competition assays, cold oligonucleotide was added to the reaction mixture in 100-fold molar excess. A double-stranded mutant GATA oligonucleotide (SEQ ID NO:10) [5'-CACTTCTTAACAGAAAGTCTTAACTCT-3'] (Santa Cruz Biotechnology) was also used as a competitor. In antibody supershift assays, two monoclonal antibodies to GATA-3 were used (#HG3-31X and #HG3-35X; Santa Cruz Biotechnology). In some experiments, 4-hydroxytamoxifen (Sigma Chemical Company) was added as 1 μl of solution in methanol to the final concentration indicated.

Immunohistochemistry.

Primary invasive breast carcinomas were examined for ER, progesterone receptor (PR) and GATA-3 expression using immunoperoxidase (IPOX). Forty seven consecutive archival formalin-fixed, paraffin-embedded breast cancer specimens were prepared for nuclear staining and automated immunohistochemistry, as described previously (van de Rijn et al. (1994) *Hum. Pathol.* 25, 766–771). Commercially available monoclonal antibodies for ER (clone 6F11) and PR (clone 1A6) were used (Ventana Medical Systems, Inc., Tucson, Ariz.). The GATA-3 monoclonal antibody (HG3-31X) was used at a dilution of 1:250 according to a manual protocol, with microwave antigen retrieval pretreatment in citrate buffer. Positive staining for all antigens was defined as staining of at least 5% of nuclei in any region.

Results

Identification of GATA-3 in Breast Carcinoma Cells.

In order to identify genes expressed in association with estrogen receptor (ER) in breast cancer, arrays of cloned cDNAs were hybridized with probes prepared from mRNA isolated from breast carcinoma cell lines discordant in ER phenotype. Two ER-positive (MCF7 and T47D) and two ER-negative (MDA-MB-231 and HBL-100) breast carcinoma cell lines were used for the initial screening procedure. RNA was isolated from each cell line and a probe representing total cDNA from each cell line was hybridized to four identical cDNA arrays. The pattern of gene expression for the cloned cDNAs on this array were extremely similar for all four cell lines, with the exception of a striking difference in the signal for position D7a. There is a strong signal with probes prepared from the ER-positive lines, MCF7 and T47D, but no hybridization detected with probes derived from the ER-negative lines, MDA-MB-231 and HBL-100. The cloned cDNA corresponding to D7a is GATA-3.

To confirm the validity of this result, Northern blots were used to examine GATA-3 expression in a panel of breast carcinoma cell lines, shown in FIG. 1. RNA from eight breast carcinoma cell lines was analyzed using probes for GATA-3, ER and Actin. There was abundant expression of GATA-3 mRNA in MCF7 and T47D but minimal or no expression detected in MDA-MB-231 and HBL-100. This result confirms the finding from the cDNA arrays. Four additional breast carcinoma cell lines discordant in ER expression were also included. There appears to be a qualitative association between GATA-3 expression and ER expression in this panel of eight cell lines. For example, BT20 expresses low levels of ER mRNA and also has low GATA-3 expression. Actin is used as a probe to provide an indication of the total amount of mRNA in each lane.

There are at least six members of the GATA family of transcription factors and regions of these genes have significant homology. Two separate experiments were performed to confirm that the identified gene is GATA-3. First, a probe was prepared from the 5' untranslated region of GATA-3 cDNA. This probe (5' GATA-3) does not have sequence homology with any of the other GATA family members. The 5' GATA-3 probe gives an identical hybridization pattern as the full-length GATA-3 cDNA. Second, an MCF7 cDNA library was screened with the GATA-3 cDNA probe which, because of highly conserved regions, could potentially hybridize to multiple GATA family members. Eight separate cDNA clones were obtained and were partially sequenced from the 5' and 3' ends. All sequences matched the published sequence for human GATA-3. These findings confirm that the gene identified in these experiments is GATA-3.

Figure 2:
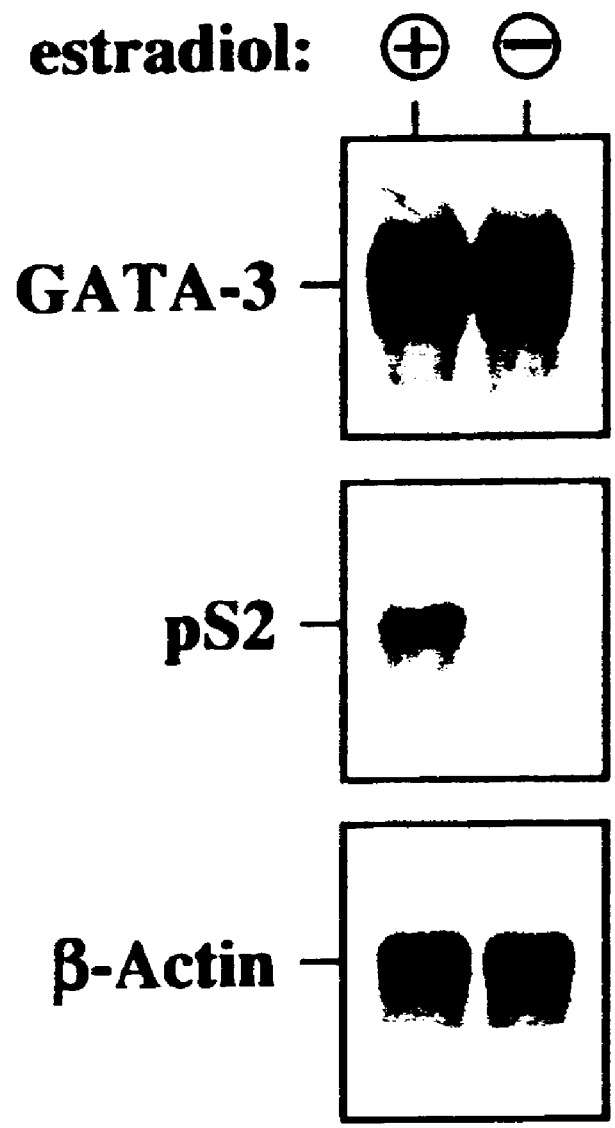
FIG. 2 is a northern blot with samples from cells in the presence and absence of estradiol.

To determine the relationship between ER and GATA-3, the response of GATA-3 to estradiol was examined. Northern blots were prepared with RNA from MCF7 cells in the presence and absence of β-estradiol, shown in FIG. 2. The expression of GATA-3 did not change with estradiol treatment. As a control, a probe for pS2 was used. The pS2 gene is known to be ER-regulated and is induced with estradiol in MCF7 cells. pS2 expression was induced with estradiol. Actin demonstrates approximately equal amounts of RNA in each lane. These results show that GATA-3 is not regulated by ER.

Functional GATA-3 Protein.

It was important to determine if functional GATA-3 protein is expressed in these cells. The GATA-3 cDNA was cloned from the MCF7 cells and GATA-3 protein was expressed using in vitro transcription/translation. GATA-3 produced by in vitro transcription/translation(TnT-GATA3) binds to the GATA-3 probe and demonstrates the appropriate sequence specificity as determined by gel shift competition. Monoclonal antibodies to GATA-3 were able to supershift the GATA-3 complex. MCF7 nuclear extracts were also tested for GATA binding activity. Sequence specific GATA binding protein was detected in MCF7 nuclear extracts. MCF7 nuclear extracts generate a complex with the appropriate sequence specificity but that migrates more slowly than the TnT-GATA3 complex. This complex does not supershift with GATA-3 specific antibody either because the complex is too large to resolve a small increase in size with antibody, or because the epitope is blocked in the complex. Nuclear extracts from HBL-100 cells do not contain GATA sequence specific complexes. These results indicate that MCF7 cells express functional GATA-3 that is present in high molecular weight complexes with appropriate sequence specific DNA binding.

Previous studies have demonstrated that GATA-1 binds to ER in a ligand-dependent fashion and tamoxifen has been shown to disrupt ER binding to GATA-1 (Blobel et al. (1995) *Mol. Cell. Biol.* 15, 3147–3153). ER may be part of the GATA-sequence specific complex in MCF7 cells. When tamoxifen was added to the complexes, it disrupted them. The $K_d$ for the tamoxifen-ER interaction is approximately 0.2 nM (Toko et al. (1992) *J.Steroid Biochem. Molec. Biol.* 43, 507–514). Tamoxifen disrupts the GATA-3 complex at a concentration consistent with high affinity ER binding. However, even at a high concentration (1 μM) tamoxifen does not interfere with free GATA-3 binding DNA. Free GATA-3 liberated from the complex binds to the GATA probe and supershifts with the GATA-3 monoclonal antibody. This free GATA-3 supershift complex from MCF7 extract co-migrates with the TNT-GATA-3 supershift complex. These results indicate that GATA-3 is present in a multiprotein complex with ER and this interaction can be disrupted by tamoxifen.

GATA-3 Expression in Primary Breast Cancer.

Figure 3:
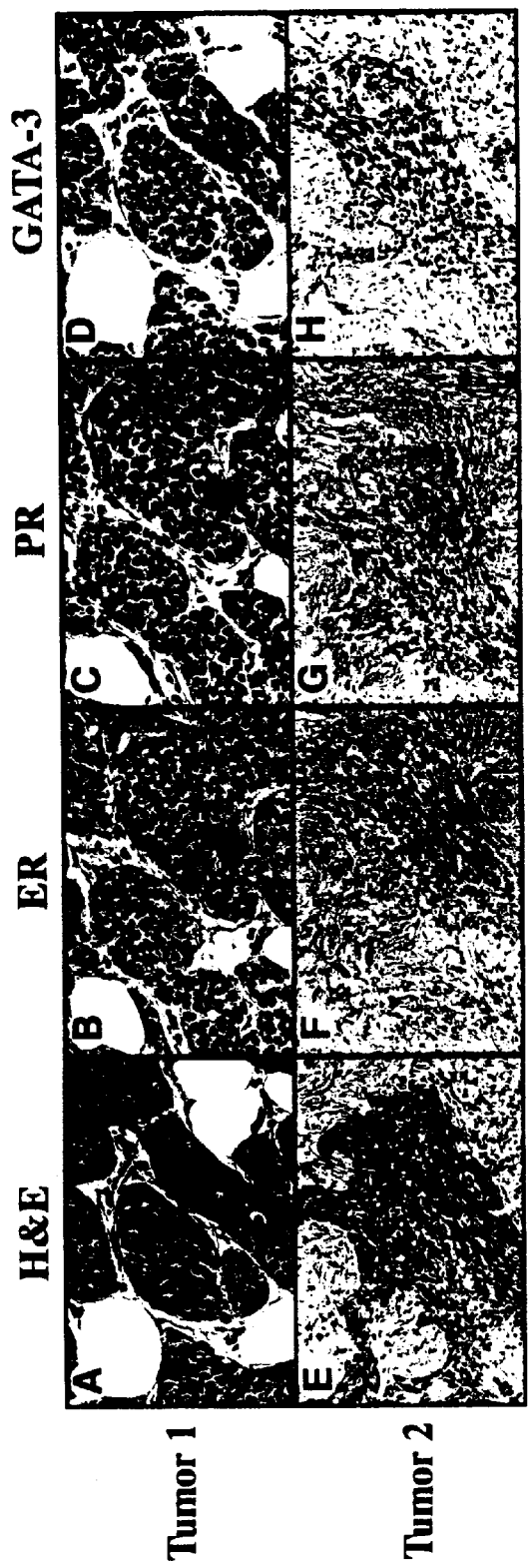
FIG. 3 illustrates the ER, PR and GATA-3 staining pattern for two representative breast cancers. Tumor 1 is an example of a breast cancer that is positive for ER, PR and GATA-3. Tumor 2 is a high-grade carcinoma that is negative for ER, PR and GATA-3.

All of the results described above were performed with breast carcinoma cell lines that have been maintained in cell culture for many years. To determine if there is an association between ER and GATA-3 in primary breast cancers, GATA-3 expression was examined on a panel of primary breast cancers using immunoperoxidase (IPOX). The monoclonal antibody used in these experiments is specific for GATA-3 and does not cross-react with the other GATA family members. ER and PR expression were also examined in these cancers using IPOX. FIG. 3 illustrates the ER, PR and GATA-3 staining pattern for two representative breast cancers. Tumor 1 is an example of a breast cancer that is positive for ER, PR and GATA-3. Tumor 2 is a high-grade carcinoma that is negative for ER, PR and GATA-3. Table 1 summarizes the results for 47 breast cancers. There is a statistically significant association between ER and GATA-3 expression in primary carcinomas ($p<0.0001$, $X^2$).

TABLE 1

| ER Phenotype | GATA-3 + | GATA-3 − |
|---|---|---|
| ER+ PR+ | 21 | 1 |
| ER+ PR− | 8 | 0 |
| Total | 29 | 1 |
| ER− PR+ | 0 | 1 |
| ER− PR− | 4 | 12 |
| Total | 4 | 13 |

Ninety-seven percent of ER-positive tumors are GATA-3 positive and 76 percent of ER-negative tumors are GATA-3 negative. These data establish a clear association between GATA-3 and the ER-positive phenotype in breast cancer.

The expression of ER in breast cancer identifies a tumor phenotype that is associated with hormone responsiveness, longer disease-free interval and longer overall survival. Previous work to elucidate the molecular basis for these clinical parameters has focused on examining ER phenotypes including ER splice variants, ER mutations and ER functional alterations of transcriptional activation. Extensive work has also included studies of ER-responsive genes such as PR and pS2. Mechanisms to alter the ER response pathway has lead to the development of an number of ER agonists and antagonists. These agents, such as tamoxifen, have provided a basis to alter the normal physiologic response of these tumors and are now in common use for the treatment of hormone responsive tumors.

ER is known to modulate the transcriptional activity of a number of factors including GATA-1, AP-1 and retinoic acid receptor (RAR). There are two studies demonstrating a direct protein-protein interaction between ER and GATA-1. This interaction was hypothesized to be the basis for the effect of estrogen repression of erythropoiesis. Also, it was demonstrated that ligand-activated ER binds to and inhibits GATA-1 in erythroid cells, inducing apoptosis. ER binds to GATA-1 in at least two places, one of which is a zinc finger domain which is conserved among GATA family members. ERα and ERβ have been shown to bind to AP-1 and this binding is ligand-dependent. In the case of ERβ, interaction with AP-1 inhibits AP-1 activity and this inhibition can be reversed with tamoxifen. Although studies demonstrating ERβ modulation of AP-1 activity are attractive, these experiments involve co-transfection into cells which do not normally express these proteins. The present finding of co-expression of ER and GATA-3 in primary tumors supports the biological and clinical relevance of an interaction between these factors.

It is important to determine the molecular basis for the coexpression of ER and GATA-3. Genes such as PR and pS2 are induced by estradiol and the association between ER and expression of these genes in breast cancer is due to regulation through estrogen response elements (EREs) in the promoters of these genes. Data concerning estradiol responsiveness in MCF7 cells argue that GATA-3 is not an ER-responsive gene. It is, therefore, particularly intriguing that the correlation between ER and GATA-3 expression is better than between ER and PR expression. GATA-3 may be responsible for establishing the hormone-responsive phenotype and may be involved in regulating ER expression. Since GATA-3 is known to be a transcription factor, the striking pattern of expression in ER-positive tumors indicates that target genes regulated by GATA-3 are integral to the hormone-responsive breast cancer phenotype. The use of breast cancer cell lines will help to elucidate targets of GATA-3 gene regulation.

In summary, a highly significant correlation between ER and (GATA-3 expression in breast cancers ($p<0.0001$, $X^2$) has been identified. GATA-3 has not previously been described in breast cancer but has been shown to be involved in the differentiation and regulation of gene expression in T lymphoid cells. In addition, in cells which express ER and GATA-3, these proteins exist in a multiprotein complex that can be disrupted by tamoxifen. These results indicate that tamoxifen may function in part through regulation of GATA-3 activity.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of phenotyping a breast carcinoma, the method comprising:

combining a sample of said breast carcinoma with a GATA-3 specific binding member;

determining the presence of complexes formed between a GATA-3 molecule and said specific binding member, wherein the presence of said complexes is indicative that said breast carcinoma has a phenotype associated with expression of the estrogen receptor.

2. A method according to claim 1, wherein said GATA-3 molecule is a nucleic acid.

3. A method according to claim 2, wherein said specific binding member is a nucleic acid probe complementary to GATA-3.

4. A method according to claim 3, wherein said probe comprises a detectable label.

5. A method according to claim 3, wherein said nucleic acid probe hybridizes the untranslated region of GATA-3 mRNA.

6. A method according to claim 1, wherein said sample is a biopsy cell sample or cells cultured therefrom.

7. A method according to claim 6, wherein said sample is a lysate of said cell sample.

* * * * *

SEQUENCE LISTING

<160> NUMBER OF SEQ ID NOS: 10

<210> SEQ ID NO 1
<211> LENGTH: 1456
<212> TYPE: DNA
<213> ORGANISM: H. sapiens
<220> FEATURE:

-continued

```
<221> NAME/KEY: CDS
<222> LOCATION: (120)...(1451)

<400> SEQUENCE: 1
aaatcattca acgaccccg accctccgac ggcaggagcc ccccgacctc ccaggcggac      60
cgcctccctc cccgcgcgcg gttccgggcc cggcgagagg gcgcgagaca gccgaggcc     119 atg gag gtg acg gcg gac cag ccg cgc tgg ttg agc cac cac cac ccc      167
Met Glu Val Thr Ala Asp Gln Pro Arg Trp Leu Ser His His His Pro
 1               5                  10                  15 gcc gtg ctc aac ggg cag cac ccg gac acg cac cac ccg ggc ctc agc      215
Ala Val Leu Asn Gly Gln His Pro Asp Thr His His Pro Gly Leu Ser
             20                  25                  30 cac tcc tac atg gac gcg gcg cag tac ccg ctg ccg gag gag gtg gat     263
His Ser Tyr Met Asp Ala Ala Gln Tyr Pro Leu Pro Glu Glu Val Asp
         35                  40                  45 gtg ctt ttt aac atc gac ggt caa ggc aac cac gtc ccg ccc tac tac     311
Val Leu Phe Asn Ile Asp Gly Gln Gly Asn His Val Pro Pro Tyr Tyr
     50                  55                  60 gga aac tcg gtc agg gcc acg gtg cag agg tac cct ccg acc cac cac     359
Gly Asn Ser Val Arg Ala Thr Val Gln Arg Tyr Pro Pro Thr His His
 65                  70                  75                  80 ggg agc cag gtg tgc cgc ccg cct ctg ctt cat gga tcc cta ccc tgg     407
Gly Ser Gln Val Cys Arg Pro Pro Leu Leu His Gly Ser Leu Pro Trp
                 85                  90                  95 ctg gac ggc ggc aaa gcc ctg ggc agc cac cac acc gcc tcc ccc tgg     455
Leu Asp Gly Gly Lys Ala Leu Gly Ser His His Thr Ala Ser Pro Trp
            100                 105                 110 aat ctc agc ccc ttc tcc aag acg tcc atc cac cac ggc tcc ccg ggg     503
Asn Leu Ser Pro Phe Ser Lys Thr Ser Ile His His Gly Ser Pro Gly
        115                 120                 125 ccc ctc tcc gtc tac ccc ccg gcc tcg tcc tcc tcc ttg tcg ggg ggc     551
Pro Leu Ser Val Tyr Pro Pro Ala Ser Ser Ser Ser Leu Ser Gly Gly
    130                 135                 140 cac gcc agc ccg cac ctc ttc acc ttc ccg ccc acc ccg ccg aag gac     599
His Ala Ser Pro His Leu Phe Thr Phe Pro Pro Thr Pro Pro Lys Asp
145                 150                 155                 160 gtc tcc ccg gac cca tcg ctg tcc acc cca ggc tcg gcc ggc tcg gcc     647
Val Ser Pro Asp Pro Ser Leu Ser Thr Pro Gly Ser Ala Gly Ser Ala
                165                 170                 175 cgg cag gac gag aaa gag tgc ctc aag tac cag gtg ccc ctg ccc gac     695
Arg Gln Asp Glu Lys Glu Cys Leu Lys Tyr Gln Val Pro Leu Pro Asp
            180                 185                 190 agc atg aag ctg gag tcg tcc cac tcc cgt ggc agc atg acc gcc ctg     743
Ser Met Lys Leu Glu Ser Ser His Ser Arg Gly Ser Met Thr Ala Leu
        195                 200                 205 ggt gga gcc tcc tcg tcg acc cac cac cca tac acc acc tac ccg cct     791
Gly Gly Ala Ser Ser Ser Thr His His Pro Tyr Thr Thr Tyr Pro Pro
    210                 215                 220 acg tgc ccc gag tac agc tcc gga ctc ttc ccc ccc agc agc ctg ctg     839
Thr Cys Pro Glu Tyr Ser Ser Gly Leu Phe Pro Pro Ser Ser Leu Leu
225                 230                 235                 240 ggc ggc tcc ccc acc ggc ttc gga tgc aag tcc agg ccc aag gcc cgg     887
Gly Gly Ser Pro Thr Gly Phe Gly Cys Lys Ser Arg Pro Lys Ala Arg
                245                 250                 255 tcc agc aca gaa ggc agg gag tgt gtg aac tgt ggg gca acc tcg acc     935
Ser Ser Thr Glu Gly Arg Glu Cys Val Asn Cys Gly Ala Thr Ser Thr
            260                 265                 270 cca ctg tgg cgg cga gat ggc acg gga cac tac ctg tgc aga cgc tgc     983
Pro Leu Trp Arg Arg Asp Gly Thr Gly His Tyr Leu Cys Arg Arg Cys
```

```
                 275                 280                 285
ggg ctc tat cac aaa atg aac gga cag aac cgg ccc ctc att aag ccc    1031
Gly Leu Tyr His Lys Met Asn Gly Gln Asn Arg Pro Leu Ile Lys Pro
        290                 295                 300 aag cga agg ctg tct gca gcc agg aga gca ggg acg tcc tgt gcg aac    1079
Lys Arg Arg Leu Ser Ala Ala Arg Arg Ala Gly Thr Ser Cys Ala Asn
305                 310                 315                 320 tgt cag acc acc aca acc aca ctc tgg agg agg aat gcc aat ggg gac    1127
Cys Gln Thr Thr Thr Thr Thr Leu Trp Arg Arg Asn Ala Asn Gly Asp
                325                 330                 335 cct gtc tgc aat gcc tgt ggg ctc tac tac aag ctt cac aat att aac    1175
Pro Val Cys Asn Ala Cys Gly Leu Tyr Tyr Lys Leu His Asn Ile Asn
            340                 345                 350 aga ccc ctg act atg aag aag gaa ggc atc cag acc aga aac cga aaa    1223
Arg Pro Leu Thr Met Lys Lys Glu Gly Ile Gln Thr Arg Asn Arg Lys
        355                 360                 365 atg tct agc aaa tcc aaa aag tgc aaa aaa gtg cat gac tca ctg gag    1271
Met Ser Ser Lys Ser Lys Lys Cys Lys Lys Val His Asp Ser Leu Glu
370                 375                 380 gac ttc ccc aag aac agc tcg ttt aac ccg gcc gcc ctc tcc aga cac    1319
Asp Phe Pro Lys Asn Ser Ser Phe Asn Pro Ala Ala Leu Ser Arg His
385                 390                 395                 400 atg tcc tcc ctg agc cac atc tcg ccc ttc agc cac tcc agc cac atg    1367
Met Ser Ser Leu Ser His Ile Ser Pro Phe Ser His Ser Ser His Met
                405                 410                 415 ctg acc acg ccc acg ccg atg cac ccg gca tcc agc ctg tcc ttt gga    1415
Leu Thr Thr Pro Thr Pro Met His Pro Ala Ser Ser Leu Ser Phe Gly
            420                 425                 430 cca cac cac ccc tcc agc atg gtc acc ggc atg ggt tagag             1456
Pro His His Pro Ser Ser Met Val Thr Gly Met Gly
        435                 440

<210> SEQ ID NO 2
<211> LENGTH: 6
<212> TYPE: DNA
<213> ORGANISM: H. sapiens

<400> SEQUENCE: 2 wgatar                                                                6

<210> SEQ ID NO 3
<211> LENGTH: 20
<212> TYPE: DNA
<213> ORGANISM: H. sapiens

<400> SEQUENCE: 3
cctggaatct cagccccttc                                                20

<210> SEQ ID NO 4
<211> LENGTH: 21
<212> TYPE: DNA
<213> ORGANISM: H. sapiens

<400> SEQUENCE: 4
gttggaacac agacaccaca g                                              21

<210> SEQ ID NO 5
<211> LENGTH: 26
<212> TYPE: DNA
<213> ORGANISM: H. sapiens

<400> SEQUENCE: 5
```

-continued

```
ccttctcctt tgctcacctt tgcttc                                    26

<210> SEQ ID NO 6
<211> LENGTH: 26
<212> TYPE: DNA
<213> ORGANISM: H. sapiens

<400> SEQUENCE: 6
ctcggctgtg ctcgcgccct ctcgcc                                    26

<210> SEQ ID NO 7
<211> LENGTH: 35
<212> TYPE: DNA
<213> ORGANISM: H. sapiens

<400> SEQUENCE: 7
ggggaattca gccgaggcca tggaggtgac ggcgg                          35

<210> SEQ ID NO 8
<211> LENGTH: 30
<212> TYPE: DNA
<213> ORGANISM: H. sapiens

<400> SEQUENCE: 8
agcctcgagc agggctctaa cccatggcgg                                30

<210> SEQ ID NO 9
<211> LENGTH: 27
<212> TYPE: DNA
<213> ORGANISM: H. sapiens

<400> SEQUENCE: 9
cacttgataa cagaaagtga taactct                                   27

<210> SEQ ID NO 10
<211> LENGTH: 27
<212> TYPE: DNA
<213> ORGANISM: H. sapiens

<400> SEQUENCE: 10
cacttcttaa cagaaagtct taactct                                   27
```